United States Patent
Goldschmidt et al.

(10) Patent No.: US 10,859,536 B2
(45) Date of Patent: Dec. 8, 2020

(54) PHOTOACOUSTIC FLOW CELL FOR IDENTIFICATION OF RARE ANALYTES IN SUSPENSION

(71) Applicant: The Curators of the University of Missouri, Columbia, MO (US)

(72) Inventors: Benjamin Samuel Goldschmidt, Columbia, MO (US); Kyle Rood, Columbia, MO (US); John Andrew Viator, Columbia, MO (US)

(73) Assignee: The Curators of the University of Missouri, Columbia, MO (US)

(*) Notice: Subject to any disclaimer, the term of this patent is extended or adjusted under 35 U.S.C. 154(b) by 32 days.

(21) Appl. No.: 15/563,490

(22) PCT Filed: Mar. 31, 2016

(86) PCT No.: PCT/US2016/025211
§ 371 (c)(1),
(2) Date: Sep. 29, 2017

(87) PCT Pub. No.: WO2016/161082
PCT Pub. Date: Oct. 6, 2016

(65) Prior Publication Data
US 2018/0088087 A1 Mar. 29, 2018

Related U.S. Application Data

(60) Provisional application No. 62/142,131, filed on Apr. 2, 2015.

(51) Int. Cl.
*G01N 29/24* (2006.01)
*G01N 29/28* (2006.01)
(Continued)

(52) U.S. Cl.
CPC ......... *G01N 29/2425* (2013.01); *G01N 21/05* (2013.01); *G01N 21/1702* (2013.01);
(Continued)

(58) Field of Classification Search
CPC ............... G01N 29/2425; G01N 21/05; G01N 21/1702; G01N 29/02; G01N 29/28
(Continued)

(56) References Cited

U.S. PATENT DOCUMENTS 4,607,145 A * 8/1986 Ravinet ................... H04R 1/04
381/190
5,144,056 A 9/1992 Lina et al.
(Continued)

FOREIGN PATENT DOCUMENTS

JP H0526627 A 2/1993

OTHER PUBLICATIONS

Acoustical impedance. (n.d.) McGraw-Hill Concise Encyclopedia of Physics. (2002). Retrieved Dec. 2, 2019 from https://encyclopedia2.thefreedictionary.com/Acoustical+impedance.*
(Continued)

*Primary Examiner* — Nimeshkumar D Patel
*Assistant Examiner* — Jean F Morello
(74) *Attorney, Agent, or Firm* — Thompson Coburn LLP; Steven M. Ritchey

(57) ABSTRACT

A photoacoustic flow cell, the components of which may be made well in advance of conducting photoacoustic analysis, comprising (a) a chamber structure that defines a chamber, a chamber inlet, and a chamber outlet, and (b) a glass test structure, at least a portion of which is supported by the chamber structure and at least a portion of which is located in the chamber, wherein the test structure comprises an
(Continued)

interior surface that defines a test passageway through which samples will be flowed when conducting the photoacoustic analysis.

21 Claims, 2 Drawing Sheets

(51) Int. Cl.
*G01N 21/17* (2006.01)
*G01N 21/05* (2006.01)
*G01N 29/02* (2006.01)
*G01N 33/487* (2006.01)
*G01N 33/49* (2006.01)

(52) U.S. Cl.
CPC .............. *G01N 29/02* (2013.01); *G01N 29/28* (2013.01); *G01N 33/487* (2013.01); *G01N 33/4915* (2013.01); *G01N 2291/022* (2013.01); *G01N 2291/02466* (2013.01); *G01N 2291/101* (2013.01)

(58) Field of Classification Search
USPC ........................................................ 73/61.48
See application file for complete search history.

(56) References Cited

U.S. PATENT DOCUMENTS

| | | | |
|---|---|---|---|
| 5,616,826 A | 4/1997 | Pellaux et al. | |
| 6,529,835 B1* | 3/2003 | Wada | B01L 3/5027 702/19 |
| 8,293,176 B2 | 10/2012 | Viator et al. | |
| 9,151,709 B2 | 10/2015 | O'Brien et al. | |
| 2001/0022657 A1 | 9/2001 | Autrey et al. | |
| 2002/0026833 A1 | 3/2002 | Autrey et al. | |
| 2002/0135771 A1* | 9/2002 | Witty | G01N 33/558 356/445 |
| 2003/0090663 A1 | 5/2003 | Autrey et al. | |
| 2007/0197886 A1* | 8/2007 | Naganuma | A61B 5/0095 600/322 |
| 2011/0112391 A1* | 5/2011 | Nishihara | A61B 5/0059 600/407 |
| 2011/0217762 A1 | 9/2011 | Viator et al. | |
| 2011/0275890 A1 | 11/2011 | Wang et al. | |
| 2012/0064566 A1 | 3/2012 | O'Brien et al. | |
| 2012/0296192 A1 | 11/2012 | Fukutani | |
| 2013/0255388 A1* | 10/2013 | Takeuchi | G01N 29/2418 73/655 |
| 2014/0039293 A1* | 2/2014 | Oraevsky | A61B 5/0095 600/407 |

OTHER PUBLICATIONS

Acoustical impedance. (n.d.) Farlex Partner Medical Dictionary. (2012). Retrieved Dec. 2 2019 from https://medical-dictionary.thefreedictionary.com/Acoustical+impedance.*
"Borosilicate Glass", CTS, Datasheet, Capillary Tube Supplies Ltd, 2014, 1 page, retreived from <URL:https://web.archive.org/web/20140825002728/http://www.capillarytubes.co.uk/acatalog/Borosilicate_Glass_Capillary_Tubes.html>.
International Search Report and Written Opinion for PCT/US2016/025211 dated Jul. 12, 2016.
Lai et al., "Capillary Flow Cell for Photoacoustic Detection of Organic Compounds", Analytical Chemistry, Dec. 1983, pp. 2441-2444, vol. 55, No. 14.
Duncan et al., "Characteristics of sound propagation in shallow water over an elastic seabed with a thin cap-rock layer", J. Acoust. Soc. Am., Jul. 2013, pp. 207-215-9, vol. 134, No. 1.
Lee et al., "Out-coupling of Longitudinal Photoacoustic Pulses by Mitigating the Phase Cancellation", Scientific Reports, Feb. 2016, pp. 1-9, vol. 6, 21511.

* cited by examiner

PHOTOACOUSTIC FLOW CELL FOR IDENTIFICATION OF RARE ANALYTES IN SUSPENSION

CROSS REFERENCE TO RELATED APPLICATIONS

The present application is a 35 U.S.C. § 371 National Phase Application of International Patent Application No. PCT/2016/025211, filed Mar. 31, 2016, claiming benefit of U.S. Provisional Application 62/142,131, filed Apr. 2, 2015, which is incorporated herein by reference in its entirety.

FIELD OF THE INVENTION

A field of the invention is medical testing. One aspect of the invention concerns devices and methods for the detection of analytes in a bodily fluid sample (e.g., circulating tumor cells in a blood sample).

BACKGROUND OF INVENTION

Detection of analytes in bodily fluid samples is widely used for medicinal and other purposes. Applications include detection of pathogens, proteins, environmental contaminants or other chemical compounds in blood, urine, bile, saliva, or other bodily fluids. Some example applications include drug screening, detection of disease, detection of a particular protein, monitoring of toxic heavy metal levels in and around bodies, flows, or sources of water (e.g., lakes, rivers, streams, seas, oceans, drainage fields, wells, and the like). By way of one particular example, detection of circulating tumor cells (CTCs) in human blood and lymph systems has the potential to aid clinical decision making in the treatment of cancer. The presence of CTCs may signify the onset of metastasis, indicate relapse, or may be used to monitor disease progression.

One particularly useful technique for detecting such CTCs involves photoacoustic detection such as set forth in U.S. patent application Ser. No. 13/110,624 (Pub. No. 2011/0217762), which is incorporated by reference herein in its entirety.

Such photoacoustic detection methods have utilized flow cells made by casting a polyacrylamide gel around a wire. After the gel is adequately set, the wire is removed thereby yielding a passageway through the gel structure through which analyte samples are flowed when performing the photoacoustic detection. There are, however, drawbacks with such polyacrylamide flow cells. In particular, they tend to lack homogeneity which is detrimental to testing reproducibility. Additionally, they are not particularly structurally stable, which necessitates extraordinary delicate handling. They are also not particularly stable over time, which necessitates that they be formed relatively shortly before performing the photoacoustic detection. Still further, they tend to be more susceptible to introducing contaminants into the analyte samples. Thus, a need exists for flow cells that remedy or minimize one or more of the above-described shortcomings.

SUMMARY OF INVENTION

In one embodiment, the present invention is directed to a photoacoustic flow cell kit for use in conducting a photoacoustic analysis of one or more samples, which comprises irradiating the sample(s) with a laser light and detecting an acoustic wave generated by a thermoelastic expansion of one or more analytes present in the sample(s) resulting from the laser light being absorbed by the analyte(s), the kit comprising:

(a) a test structure, which comprises an interior surface that defines a test passageway through which the sample(s) will be flowed when conducting the photoacoustic analysis, wherein the test structure (i) comprises a test structure material that transmits the laser light and has an acoustic impedance that is substantially different from the acoustic impedance of the sample(s) and (ii) is configured so that the acoustic wave passes through the test structure without being substantially reflected due to the difference between the acoustic impedances; and (b) a chamber structure configured to (i) define a chamber, a chamber inlet, and a chamber outlet and (ii) to locate at least a portion of the test structure in the chamber when conducting the photoacoustic analysis.

In another embodiment, the present invention is directed to a photoacoustic flow cell assembled with the aforementioned kit.

In yet another embodiment, the present invention is directed to a photoacoustic flow cell for use in conducting a photoacoustic analysis of one or more samples, which comprises irradiating the sample(s) with a laser light and detecting an acoustic wave generated by a thermoelastic expansion of one or more analytes present in the sample(s) resulting from the laser light being absorbed by the analyte(s) with an acoustic sensor, the photoacoustic flow cell comprising:

(a) a chamber structure that defines a chamber, a chamber inlet, and a chamber outlet, wherein either (i) a portion of the chamber structure that defines the chamber is an acoustic wall through which the acoustic wave passes through and that is contact with the acoustic sensor, which is located outside of the chamber, or (ii) the chamber structure is configured to locate the acoustic sensor inside of the chamber; and (b) a test structure, at least a portion of which is supported by the chamber structure and at least a portion of which is located in the chamber, wherein the test structure comprises an interior surface that defines a test passageway that passes through, or is in fluid communication with or through, the chamber inlet and outlet and through which the sample(s) will be flowed when conducting the photoacoustic analysis, wherein the test structure comprises a test structure material that comprises a glass that transmits the laser light and has a wall thickness in a range of about 5 μm to about 50 μm.

In still another embodiment, the present invention is directed to a system for conducting photoacoustic analysis comprising:

(a) a first fluid tube containing a first fluid and a second fluid tube containing a second fluid, wherein the first fluid and second fluids are immiscible;

(b) a connector in fluid connection with first fluid tube, the second fluid tube, and a common tube, such that when conducting the photoacoustic analysis the first and second fluids are flowed from the first and second fluid tubes, respectively, into the connector such that alternating discrete samples of the first fluid and the second fluid flow into the common tube;

(c) the above-described photoacoustic flow cell, wherein the test passage is in fluid connection with the common tube;

(d) an acoustic sensor, if it is not provided with the photoacoustic flow cell; and (e) a laser for irradiating the alternating discrete samples in the test structure of the photoacoustic flow cell with laser light when conducting the photoacoustic analysis, wherein the laser light is absorbed by one or more analytes, if present in the samples, inducing a thermoelastic expansion the analyte(s) thereby producing an acoustic wave to be detected by the acoustic sensor.

DETAILED DESCRIPTION OF INVENTION

Figure 1:
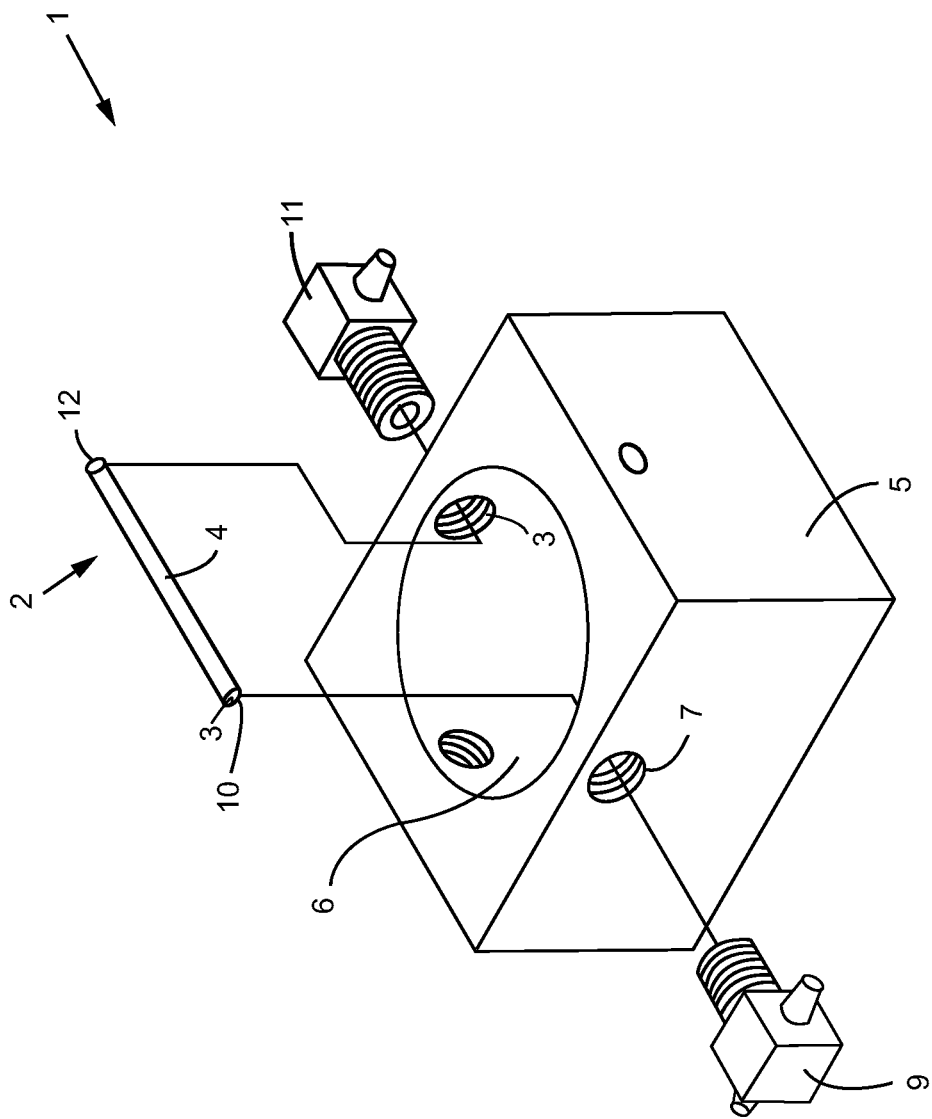
FIG. 1 is a diagram of an embodiment of a photoacoustic flow cell of the present invention.
Figure 2:
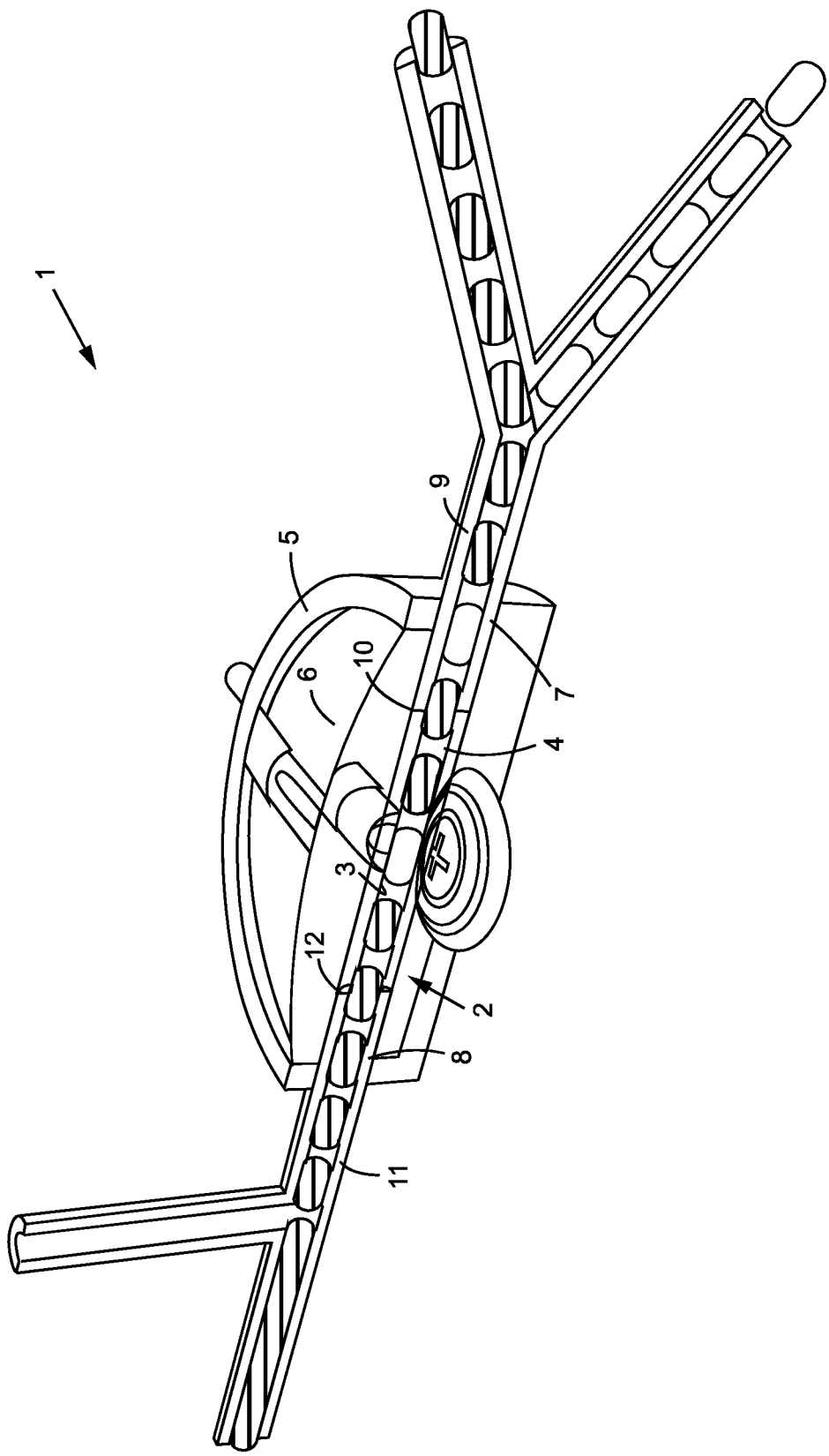
FIG. 2 is a diagram of an embodiment of a photoacoustic flow cell of the present invention.

Referring to FIGS. 1 and 2, which depict differing embodiments of the present invention, a photoacoustic flow cell 1 of the present invention may be provided as pre-made flow cell, or as components of a kit for assembling the flow cell, or as fully or partially assembled kits. For ease of discussion, however, the various embodiments of such photoacoustic flow cells will primarily be in terms of a pre-made or assembled flow cell.

As indicated above, the photoacoustic flow cell 1 is for use in conducting a photoacoustic analysis of one or more discrete samples and/or a sample portion(s) of a continuous or intermittent flow of material (e.g., flow of water for environmental testing), wherein the photoacoustic analysis comprises irradiating the sample(s) or sample portion(s) with a laser light and detecting an acoustic wave generated by a thermoelastic expansion of one or more analytes present in the sample(s) or sample portion(s) resulting from the laser light being absorbed by the analyte(s). More particularly, when conducting photoacoustic analysis, the analyte samples are excited with the laser light while within the test structure 2 of the present flow cell. As set forth above and as used hereafter, the terms "sample" or "samples" are intended to include one or more discrete samples and one or more sample portions of a continuous or intermittent flow of material.

Test Structure

Rather than selecting a transparent material of comparatively little rigidity and/or strength as polyacrylamide to make a flow cell monolith with a passage therethrough that is relatively non-uniform in orientation, dimensions, and/or surface morphology, the flow cell 1 of the present invention comprises a test structure 2 that may be configured (in terms of materials and/or dimensions) to be comparatively rigid, stronger, and/or uniform. In particular, the test structure 2 comprises an interior surface 3 that defines a test passageway 4 through which the sample(s) will be flowed when conducting the photoacoustic analysis. Additionally, the test structure, including the test passageway therethrough, may be formed well in advance of conducting the photoacoustic detection procedure.

More specifically, at least a portion of the test structure 2 comprises a test structure material that transmits the laser light. Counterintuitively, however, the test structure material has an acoustic impedance that is substantially different from the acoustic impedance of the sample(s). This is counterintuitive because previous flow cell materials, including polyacrylamide, were selected, in large part, to have an acoustic impedance similar to that of the sample(s) to facilitate transmission of the acoustic wave through the flow cell to be detected by an acoustic sensor, which must be positioned a distance away from the sample so as to not interfere with the transmission of the laser light. Whereas, placing materials of substantially different acoustic impedances adjacent to each would generally be considered to be undesirable because a substantial difference between acoustic impedances tends to cause acoustic waves to be substantially or even entirely reflected at the boundary.

Exemplary test structure materials include glasses such as fused silica and borosilicate glasses, or combinations of different glasses. Glasses typically have an acoustic impedance (Z) in a range of about 10 Mrayls to about 15 Mrayls at a frequency of about 10 MHz. Whereas the sample(s) being subjected to photoacoustic analysis, which primarily comprise liquids (aqueous and non-aqueous), have an acoustic impedance in a range of about 1.3 Mrayls to about 1.7 Mrayls at a frequency of about 10 MHz. For reference, the polymers used to make conventional flow cells have an acoustic impedance in a range of about 2 Mrayls to about 5 Mrayls at a frequency of about 10 MHz.

Utilizing a glass as the test structure material (along with other components of the photoacoustic flow cell and/or used with conducting photoacoustic analysis) provides an additional benefit in terms of enhancing the sensitivity and accuracy of the photoacoustic analysis. Photoacoustic detection is very sensitive, even to small dirt particles in the air and/or samples, and therefore it is incredibly important to keep the flow cell and relevant photoacoustic equipment very clean and possibly even sterilized. Advantageously, glass is readily cleaned (e.g., with ethylene oxide) and sterilized (e.g., with an autoclave) and it is resistant to leaching, so, it is less likely that contaminants may leach into samples than, for example, from plastics.

Although the test structure material has an acoustic impedance that is substantially different from that of the sample(s), the test structure is configured so that the acoustic wave passes through the test structure without being substantially reflected due to the thinness of the chamber material (e.g., 10 μm). For a test structure material having an acoustic impedance (Z) in a range of about 10 Mrayls to about 15 Mrayls at a frequency of about 10 MHz, the thickness of the test structure material is relatively thin (i.e., thinner than the characteristic acoustic wavelength) so that the aforementioned acoustic impedance difference does not substantially reflect the acoustic wave and it passes through the test structure. In particular, the wall thickness of the test structure is in a range of about 5 μm to about 50 μm. In another embodiment, the wall thickness is in a range of about 10 μm to about 30 μm.

Additionally, it is desirable to control the cross-sectional size or area of the test passageway so that the samples are efficiently and effectively transported therethrough. For example, for a tubular test structure, the cross-section area is circular and is in a range of about 0.008 mm$^2$ to about 20 mm$^2$, which generally corresponds to the tubular test structure having a maximum cross-sectional width or diameter in a range of about 0.1 mm to about 5 mm. In one embodiment, the test structure is tubular and the cross-sectional area is circular and is in the range of about 0.08 mm$^2$ to about 7 mm$^2$, which generally corresponds to the test structure having a maximum cross-sectional width or diameter in a range of about 1 mm to about 3 mm. In another embodiment, the test structure is tubular with a wall thickness of about 10 μm and the cross-section area is circular and is in the range of about 1.75 mm$^2$, which generally corresponds to the tubular test structure having a maximum cross-sectional width or diameter of about 1.5 mm.

In one embodiment, the test structure is a fused quartz tube that is readily available (e.g., x-ray diffraction tubes) that may be cut to an appropriate length using any appropriate method (e.g., laser or chemical etching due to the delicate nature of the tubes).

Hydrophobic Coating

The test structure (along with other components in contact with samples when conducting photoacoustic analysis such as tubing and connections) may comprise one or more coatings that impart a particular functionality. Of particular interest is imparting hydrophobicity and/or oleophobicity to the interior surface of the test structure to prevent or minimize the likelihood of samples sticking within the test passageway. This may be accomplished by, for example, forming a hydrophobic and/or oleophobic coating on the test structure material (i.e., the interior of the test structure thereby creating a hydrophobic, oleophobic, or hydrophobic-oleophobic interior surface that defines the test passageway). Exemplary, hydrophobic coatings may be formed using one or more materials such as bovine serum albumin and polysiloxane. Certain fluorocarbon compounds and/or fluoropolymers may be used to form coatings that are both hydrophobic and oleophobic, and may provide lubricity (e.g., high molecular weight perfluoropolyether trimethoxysilane, di-podal perfluoropolyether triethoxysilane, Tetrapodal perfluoropolyether triethoxysilane, and polytetrafluoroethylene).

Chamber Structure

Although a glass tube is relatively rigid, because of the small size of the test structure, it may be relatively easily damaged if subjected to even a relatively moderate amount of force. As such, it is desirable for the test structure to be secured or attached to, or supported by the above-described chamber structure 5 which tends to isolate or protect the test structure thereby allowing for convenient handling methods during use and/or transportation. The chamber structure 5 also defines a chamber 6, a chamber inlet 7, and a chamber outlet 8 and locates at least a portion of the test structure 2 in the chamber 6 when conducting the photoacoustic analysis.

The test structure 2 and the chamber structure 5 may be placed in contact, or secured, to each other through any appropriate method. For example, the test structure may be molded into a polymeric (e.g., acrylic) chamber structure. Alternatively, the test structure and the chamber structure may be secured via an interference fit as depicted in FIG. 2. Still further, the test structure and the chamber structure may be secured via connectors as depicted in FIG. 1. As shown in FIG. 1, an inlet connector 9 is configured to sealingly connect with the chamber inlet 7 and an inlet end 10 of the test structure 2 and an outlet connector 11 is configured to sealingly connect with the chamber outlet 8 and an outlet end 12 of the test structure 2 thereby providing fluid communication through the chamber inlet 7, the test passageway 4, and the chamber outlet 8.

Other Chamber Configurations and Features

The chamber may be configured and/or designed to comprise a wide variety of other features or alternative features depending upon the particular application or conditions in which the photoacoustic flow cell is to be used. For example, the chamber structure may be a single piece design (e.g., FIG. 2) or it may be a multi-component design (e.g., FIG. 1).

Further, in one embodiment, the chamber structure is configured in a particular manner because the acoustic sensor (described in more detail below) is to be located outside the chamber. In such an embodiment, a portion of the chamber structure that defines the chamber is an acoustic wall for supporting an acoustic sensor outside of the chamber. In one embodiment, the acoustic wall comprises an acoustic wall material that has an acoustic impedance that is similar to the acoustic impedance of the sample(s). For example, the acoustic wall material may be an optically transparent polymer film. In another embodiment, the acoustic wall material has an acoustic impedance that is substantially different from the acoustic impedance of the sample(s). Any potential consequences of the differing acoustic impedance are negated or mitigated by configuring the acoustic wall such that the acoustic wave passes through without being substantially reflected due to the difference between the acoustic impedances. For example, if the acoustic wall material is an aluminum foil or sheet, it preferably has a thickness in a range of about 5 µm to about 50 µm. One benefit of a non-visually transparent material is that it allows for easy visual verification of proper sample-laser alignment by an operator.

In a different embodiment, the chamber structure is configured to locate the acoustic sensor inside of the chamber. If mounted on an interior surface of the chamber, the material to which it is mounted (i.e., making upon the interior surface) is not particularly significant and visual transparency and/or acoustic reflection are essentially irrelevant.

Additionally, the flow cell may comprise one or more check valves that are located outside the chamber and placed in fluid communication with the test passageway when conducting the photoacoustic analysis. These valves allow for easier management of the fluid transport of samples.

Still further, the flow cell may comprise a cover configured to further define the chamber when conducting the photoacoustic analysis. If the laser source and the flow cell are arranged relative to each other such that the laser light would need to be transmitted through the cover, the cover will comprise a cover material that transmits the laser light. On other embodiments (with or without a cover), the laser and flow cell may be arranged such that a transparent cover would not be necessary. For example, as depicted in FIG. 2, the laser light is being transmitted through the side of the flow cell, rather than from above the flow cell.

Acoustic Sensor

As indicated above, the flow cell comprises at least one acoustic sensor for detecting sound waves generated by the rapid expansion associated with the absorption of laser light by an analyte in a sample. The particulars of the acoustic sensor(s) may be selected depending upon what is desirable for a particular application. For example, the acoustic sensor may be a non-focused acoustic sensor or a focused acoustic sensor or a combination of the two. Exemplary acoustic sensors include a polyvinylidene flouride sensor, a lithium niobate sensor, and a lead zirconium titanate sensor. In fact, various combinations of said sensor may be included. In one embodiment, the acoustic sensor comprises a focused acoustic sensor having a focus (e.g., a focal length of about 0.5 inches or 12.5 mm) that is in the chamber when conducting the photoacoustic analysis (regardless of whether inside or outside the chamber). In another embodiment, the acoustic sensor comprises a focused acoustic sensor having a focus that is not in the chamber when conducting the photoacoustic analysis. Although it is counterintuitive to use a sensor out of focus, it has been discovered that by doing so essentially the entire irradiated volume of the chamber is encompassed by the sensor.

Acoustic Wave Transmission Medium

As indicated above, the flow cell also comprises a quantity of an acoustic wave transmission medium having an acoustic impedance substantially similar to that of the sample(s), wherein the acoustic wave transmission medium is present in the chamber when conducting said photoacoustic analysis to facilitate the propagation of the acoustic wave from the test structure through the chamber. The acoustic wave transmission medium is selected from the group consisting of water, saline, water-based gel, gelatin, polyacrylamide, ultrasound gel, oil, rubber-like tissue phantom, and combinations thereof. An exemplary tissue phantom material is porcine gel.

System for Conducting Photoacoustic Analysis

As is apparent, the above-described flow cell may be incorporated in a system for conducting photoacoustic analysis. Such a system typically comprises a first fluid tube containing a first fluid and a second fluid tube containing a second fluid, wherein the first fluid and second fluids are immiscible; a connector in fluid connection with first fluid tube, the second fluid tube, and a common tube, such that when conducting the photoacoustic analysis the first and second fluids are flowed from the first and second fluid tubes, respectively, into the connector such that alternating discrete samples of the first fluid and the second fluid flow into the common tube. The test passage of any of the above-described the photoacoustic flow cells is in fluid connection with the common tube. The system comprises an acoustic sensor if it is not provided with photoacoustic flow cell. The system further comprises a laser for irradiating the alternating discrete samples in the test structure of the photoacoustic flow cell with laser light when conducting the photoacoustic analysis, wherein the laser light is absorbed by one or more analytes, if present in the samples, inducing a thermoelastic expansion the analyte(s) thereby producing an acoustic wave to be detected by the acoustic sensor.

Further exemplary information regarding photoacoustic testing, including methods, equipment, and materials are disclosed in U.S. patent applicaiton Ser. No. 13/228,428, filed Sep. 8, 2011, by O'Brien et al. entitled "Multiple Phase Flow System for Detecting and Isolating Substances," which is incorporated by reference herein in its entirety.

Having illustrated and described the principles of the present invention, it should be apparent to persons skilled in the art that the invention can be modified in arrangement and detail without departing from such principles.

Although the materials and methods of this invention have been described in terms of various embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A photoacoustic flow cell kit for use in conducting a photoacoustic analysis of one or more samples, which comprises irradiating the sample(s) with a laser light and detecting an acoustic wave generated by a thermoelastic expansion of one or more analytes present in the sample(s) resulting from the laser light being absorbed by the analyte(s), the kit comprising:
   (a) a test structure, which comprises an interior surface that defines a test passageway through which the sample(s) will be flowed when conducting the photoacoustic analysis, wherein the test structure (i) comprises a test structure material that transmits the laser light and has an acoustic impedance that is substantially different from the acoustic impedance of the sample(s), wherein the test structure material has an acoustic impedance (Z) in a range of about 2 Mrayls to about 15 Mrayls at a frequency of 10 MHz, and (ii) is configured so that the acoustic wave passes through the test structure without being substantially reflected due to the difference between the acoustic impedances, wherein the test structure is configured to have a wall thickness in a range of about 5 µm to about 50 µm; and
   (b) a chamber structure configured to (i) define a chamber, a chamber inlet, and a chamber outlet and (ii) to locate at least a portion of the test structure in the chamber when conducting the photoacoustic analysis.

2. The kit of claim 1, wherein the test structure material is selected from the group consisting of fused quartz, borosilicate glass, and combinations thereof.

3. The kit of claim 2, wherein the test structure material comprises fused quartz, and wherein test structure is configured to have a maximum cross-sectional width in a range of about 0.1 mm to about 5 mm.

4. The kit of claim 1, wherein the interior surface of the test structure is hydrophobic and oleophobic.

5. The kit of claim 1, wherein the chamber structure is a single piece design or a multi-component design.

6. The kit of claim 5, wherein a portion of the chamber structure that defines the chamber is an acoustic wall for supporting an acoustic sensor outside of the chamber, wherein the acoustic sensor detects the acoustic waves when conducting the photoacoustic analysis.

7. The kit of claim 6, wherein the acoustic wall comprises an acoustic wall material that has an acoustic impedance that is similar to the acoustic impedance of the sample(s), and wherein the acoustic wall material is an optically transparent polymer film.

8. The kit of claim 6, wherein the acoustic wall comprises an acoustic wall material that has an acoustic impedance that is substantially different from the acoustic impedance of the sample(s) and is configured so that the acoustic wave passes through the acoustic wall without being substantially reflected due to the difference between the acoustic impedances, wherein the acoustic wall material is an aluminum foil or sheet, and wherein the acoustic wall material is an aluminum foil or sheet having a thickness in a range of about 5 µm to about 50 µm.

9. The kit of claim 5, wherein the chamber structure is further configured to locate an acoustic sensor inside of the chamber, wherein the acoustic sensor detects the acoustic waves when conducting the photoacoustic analysis.

10. The kit of claim 1 further comprising an inlet connector configured to sealingly connect with the chamber inlet and an inlet end of the test structure and an outlet connector configured to sealingly connect with the chamber outlet and an outlet end of the test structure thereby providing fluid communication through the chamber inlet, the test passageway, and the chamber outlet.

11. The kit of claim 1, further comprising the acoustic sensor wherein the acoustic sensor is a non-focused acoustic sensor and/or a focused acoustic sensor selected from the group consisting of a polyvinylidene flouride sensor, a lithium niobate sensor, a lead zirconium titanate sensor, and combinations thereof.

12. The kit of claim 11, wherein the acoustic sensor is a focused acoustic sensor selected or configured to have a focus that is in the chamber when conducting the photoacoustic analysis.

13. The kit of claim 11, wherein the acoustic sensor is a focused acoustic sensor selected or configured to have a focus that is not in the chamber when conducting the photoacoustic analysis.

14. The kit of claim 1 further comprising one or more check valves that are located outside the chamber and placed in fluid communication with the test passageway when conducting the photoacoustic analysis.

15. The kit of claim 1 further comprising a quantity of an acoustic wave transmission medium having an acoustic impedance substantially similar to that of the sample(s), wherein the acoustic wave transmission medium is present in the chamber when conducting said photoacoustic analysis to facilitate the propagation of the acoustic wave from the test structure through the chamber, wherein the acoustic wave transmission medium is selected from the group consisting of water, saline, water-based gel, gelatin, polyacrylamide, ultrasound gel, oil, tissue phantom, and combinations thereof.

16. The kit of claim 1 further comprising a cover configured to further define the chamber when conducting the photoacoustic analysis, wherein the cover comprises a cover material that transmits the laser light.

17. A photoacoustic flow cell assembled with the kit of claim 1.

18. A photoacoustic flow cell for use in conducting a photoacoustic analysis of one or more samples, which comprises irradiating the sample(s) with a laser light and detecting an acoustic wave generated by a thermoelastic expansion of one or more analytes present in the sample(s) resulting from the laser light being absorbed by the analyte(s) with an acoustic sensor, the photoacoustic flow cell comprising:
(a) a chamber structure that defines a chamber, a chamber inlet, and a chamber outlet, wherein either (i) a portion of the chamber structure that defines the chamber is an acoustic wall through which the acoustic wave passes through and that is in contact with the acoustic sensor, which is located outside of the chamber, or (ii) the chamber structure is configured to locate the acoustic sensor inside of the chamber; and
(b) a test structure, at least a portion of which is supported by the chamber structure and at least a portion of which is located in the chamber, wherein the test structure comprises an interior surface that defines a test passageway that passes through, or is in fluid communication with or through, the chamber inlet and outlet and through which the sample(s) will be flowed when conducting the photoacoustic analysis, wherein the test structure comprises a test structure material that comprises a glass that transmits the laser light and has a wall thickness in a range of about 5 μm to about 50 μm, wherein the test structure material has an acoustic impedance (Z) in a range of about 2 Mrayls to about 15 Mrayls at a frequency of 10 MHz.

19. The photoacoustic flow cell of claim 18, wherein the test structure is tubular and has a maximum cross-sectional width in a range of about 0.1 mm to about 5 mm.

20. The photoacoustic flow cell of claim 18 further comprising:
the acoustic sensor;
an inlet connector sealingly connected with the chamber inlet and an inlet end of the test structure;
an outlet connector sealingly connected with the chamber outlet and an outlet end of the test structure;
one or more check valves that are located outside the chamber and in fluid communication with the test passageway;
a quantity of an acoustic wave transmission medium in the chamber to facilitate the propagation of the acoustic wave from the test structure through the chamber, wherein the acoustic wave transmission medium is selected from the group consisting of water, saline, water-based gel, gelatin, polyacrylamide, ultrasound gel, oil, tissue phantom, and combinations thereof; and
a cover that further defines the chamber.

21. A system for conducting photoacoustic analysis comprising:
(a) a first fluid tube containing a first fluid and a second fluid tube containing a second fluid, wherein the first fluid and second fluids are immiscible;
(b) a connector in fluid connection with first fluid tube, the second fluid tube, and a common tube, such that when conducting the photoacoustic analysis the first and second fluids are flowed from the first and second fluid tubes, respectively, into the connector such that alternating discrete samples of the first fluid and the second fluid flow into the common tube;
(c) the photoacoustic flow cell of claim 18, wherein the test passage is in fluid connection with the common tube;
(d) an acoustic sensor, if it is not provided with the photoacoustic flow cell; and
(e) a laser for irradiating the alternating discrete samples in the test structure of the photoacoustic flow cell with laser light when conducting the photoacoustic analysis, wherein the laser light is absorbed by one or more analytes, if present in the samples, inducing a thermoelastic expansion the analyte(s) thereby producing an acoustic wave to be detected by the acoustic sensor.

* * * * *